(12) United States Patent
SooHoo

(10) Patent No.: US 11,191,569 B2
(45) Date of Patent: Dec. 7, 2021

(54) MULTI-COMPONENT SYSTEM FOR MANIPULATION OF BONE AND SOFT TISSUES

(71) Applicant: THE REGENTS OF THE UNIVERSITY OF CALIFORNIA, Oakland, CA (US)

(72) Inventor: Nelson F. SooHoo, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/810,450

(22) Filed: Nov. 13, 2017

(65) Prior Publication Data

US 2018/0132899 A1    May 17, 2018

Related U.S. Application Data

(60) Provisional application No. 62/421,608, filed on Nov. 14, 2016.

(51) Int. Cl.

| | |
|---|---|
| *A61B 17/66* | (2006.01) |
| *A61B 34/00* | (2016.01) |
| *A61B 90/50* | (2016.01) |
| *A61B 46/10* | (2016.01) |
| *A61B 17/88* | (2006.01) |
| *A61B 17/00* | (2006.01) |
| *A61B 17/56* | (2006.01) |
| *A61B 46/00* | (2016.01) |

(52) U.S. Cl.
CPC .......... *A61B 17/66* (2013.01); *A61B 17/8866* (2013.01); *A61B 34/70* (2016.02); *A61B 46/10* (2016.02); *A61B 90/50* (2016.02); *A61B 46/00* (2016.02); *A61B 2017/00212* (2013.01); *A61B 2017/00221* (2013.01); *A61B 2017/564* (2013.01)

(58) Field of Classification Search
CPC ..... A61B 17/60; A61B 17/64; A61B 17/6416; A61B 17/6441; A61B 17/6458; A61B 17/6466; A61B 17/66; A61B 34/00; A61B 34/30; A61B 2034/305; A61B 17/6425; A61B 90/50

See application file for complete search history.

(56) References Cited

U.S. PATENT DOCUMENTS

| | | | |
|---|---|---|---|
| 8,005,571 B2 * | 8/2011 | Sutherland | A61B 34/77 700/248 |
| 9,301,783 B2 * | 4/2016 | Gerold | A61B 17/64 |
| 2012/0083768 A1 * | 4/2012 | Skora | A61B 46/10 606/1 |

* cited by examiner

*Primary Examiner* — Eduardo C Robert
*Assistant Examiner* — Christina Negrellirodriguez
(74) *Attorney, Agent, or Firm* — Riverside Law LLP

(57) ABSTRACT

The present invention relates to devices for manipulation of bones and their associated soft-tissue structures including joints, muscles, tendons, ligaments, and nervous tissues. The devices use articulated arms that attach to bone and soft tissue to properly align bone and soft tissue for fixation. Locking members attached to the articulated arms are activated by buttons or switches to unlock the articulated arms for adjustment of the position of an attached bone and to lock the articulated arms for holding an attached bone in a stable position.

18 Claims, 6 Drawing Sheets

| 102 | Providing a first articulated arm |
| 104 | Engaging a first fragment of a fractured bone to the tissue fixing member of the first articulated arm |
| 106 | Locking the hinge of the first articulated arm |
| 108 | Providing a second articulated arm |
| 110 | Engaging a second fragment of a fractured bone to the tissue fixing member of the second articulated arm |
| 112 | Aligning the second fragment with the first fragment |
| 114 | Locking the hinge of the second articulated arm |

Figure 6

MULTI-COMPONENT SYSTEM FOR MANIPULATION OF BONE AND SOFT TISSUES

CROSS-REFERENCE TO RELATED APPLICATIONS

This application claims priority to U.S. Provisional Patent Application No. 62/421,608, filed Nov. 14, 2016, the contents of which are incorporated by reference herein in its entirety.

BACKGROUND OF THE INVENTION

In orthopedic surgery, common types of procedures include fixation of bone and soft tissues as well as reconstruction of degenerated or damaged bone and soft-tissues. Currently, surgical manipulation of these bone and soft tissues is accomplished with the application of manual force, including pressing directly on the injured limb with a mallet or metal tool, pulling on the arm or leg with a looped towel, manually holding pins placed in the bone, and simply having an assistant grasp the injured limb and pull forcefully.

The current methods of performing orthopedic surgery have several disadvantages. One disadvantage is that manual force is limited by the strength and endurance of the surgeon and surgical assistants. This limits both the magnitude of manipulation and duration of holding manipulated bone and soft tissue in specific positions. Another disadvantage is that manual manipulation has limited precision based on the ability of the surgeon and surgical assistants to position bone and soft tissue reliably with manual force.

Current techniques traumatize patients with already injured soft tissues, require assistants whose steadiness and grip weaken with fatigue, and are frustrating to the surgeon due to the lack of precision.

Thus, there is a need in the art for improved devices for manipulation of bone and soft tissue that improves strength, endurance, and precision. The present invention meets this need.

SUMMARY OF THE INVENTION

The present invention relates to a device for stably manipulating bone and soft tissue, comprising: an articulated arm comprising a first elongate shaft having a proximal and a distal end, a second elongate shaft having a proximal end and a distal end, and a hinge connecting the proximal end of the first shaft to the distal end of the second shaft; a tissue fixing member attached to the first shaft by a ball joint; and a locking member attached to the hinge; wherein the locking member is capable of locking the hinge.

In one embodiment, the proximal end of the second shaft is connected to a stable frame by a ball joint. In one embodiment, the proximal end of the second shaft is connected to one or more elongate shafts by one or more hinges, each hinge having a locking member attached thereto.

In one embodiment, the locking member is controlled by at least one button. In one embodiment, the locking member is controlled by at least one touch sensor. In one embodiment, the locking member is controlled by at least one squeezable grip.

In one embodiment, the locking member is capable of locking the hinge and the ball joint simultaneously. In one embodiment, the locking member is capable of locking the hinge and the ball joint individually. In one embodiment, the locking member comprises a potentiometer or a pressure sensor. In one embodiment, the locking member is capable of modulating the resistance in the hinge and the ball joint.

In one embodiment, the locking member comprises a lock selected from the group consisting of a twist lock, a geared knob, a clamp, an electromagnet, a drum brake, a disc brake, a clasp brake, and a band brake. In one embodiment, the tissue fixing member is selected from the group consisting of a screw, a nail, a pin, a plate, a K-wire, a clamp, a vice, and strap.

In one embodiment, the hinge and ball joint are motorized. In one embodiment, the locking, unlocking, and repositioning of the articulated arm is linked to the locking, unlocking, and repositioning of one or more additional articulated arms, such that locking, unlocking, and repositioning of one of the articulated arms is mirrored in each of the linked articulated arms. In one embodiment, the motorized hinge and ball joint respond to externally induced movement of the articulated arm to supplement the positioning of the articulated arm. In one embodiment, the motorized hinge and ball joint are remotely controllable.

In one embodiment, the device further comprises a sterile drape. In one embodiment, the device further comprises a holder capable of attaching a surgical instrument.

In another aspect, the present invention relates to a method of aligning a fractured bone; comprising the steps of: providing a first articulated arm of the present invention; engaging a first fragment of a fractured bone to the tissue fixing member of the first articulated arm; locking the hinge of the first articulated arm; providing a second articulated arm of the present invention; engaging a second fragment of the fractured bone to the tissue fixing member of the second articulated arm; aligning the second fragment with the first fragment; and locking the hinge of the second articulated arm.

In one embodiment, the method further comprises the steps of: providing one or more articulated arms of the present invention; engaging one or more fragments of the fractured bone to the tissue fixing member of each of the one or more articulated arms; aligning the one or more fragments with the first and the second fragments; and locking the hinges of each of the one or more articulated arms.

BRIEF DESCRIPTION OF THE DRAWINGS

The following detailed description of exemplary embodiments of the invention will be better understood when read in conjunction with the appended drawings. It should be understood, however, that the invention is not limited to the precise arrangements and instrumentalities of the embodiments shown in the drawings.

FIG. 6 is a flowchart of an exemplary method of using articulated arms to align a fractured bone.

DETAILED DESCRIPTION

Figure 1:
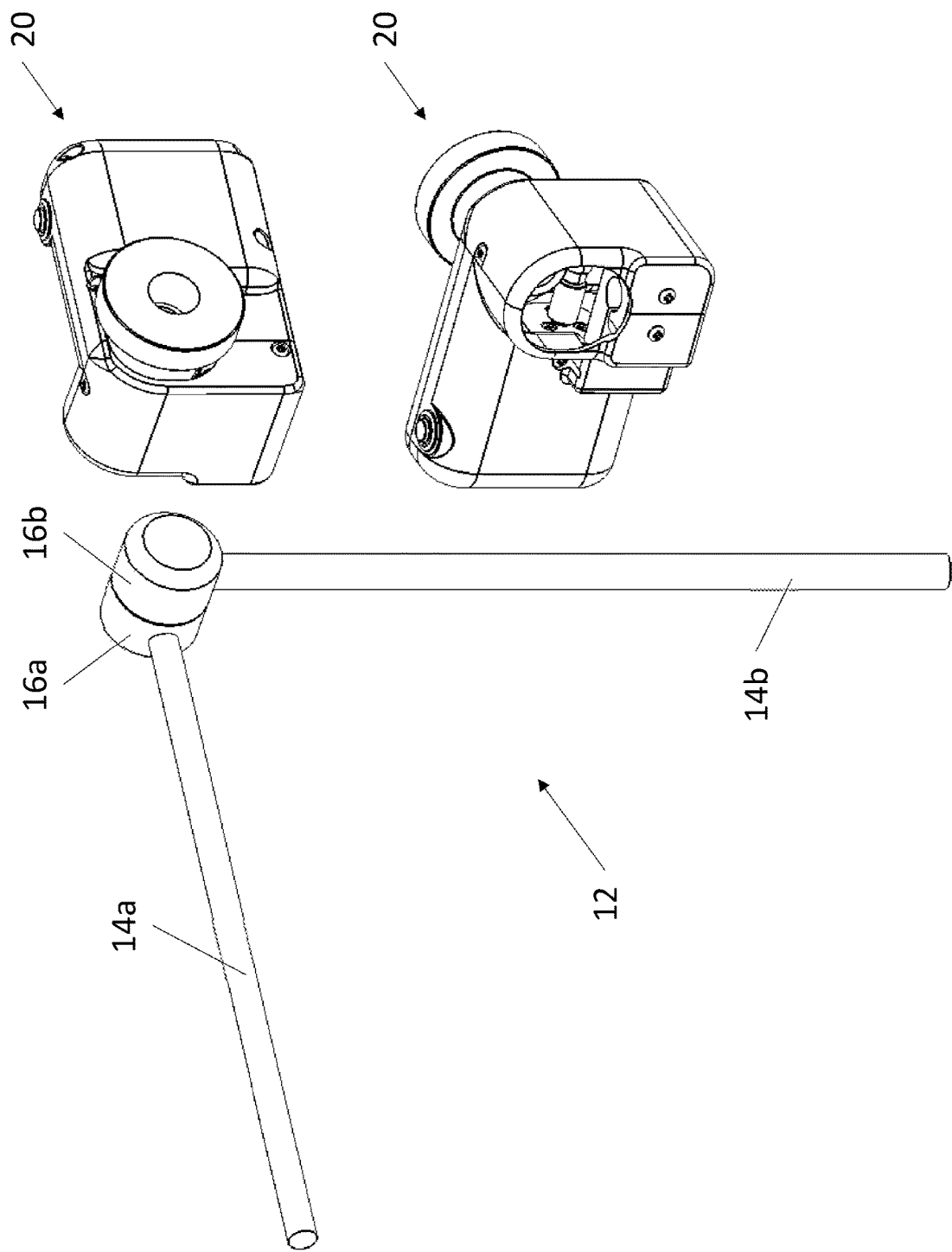
FIG. 1 depicts a diagram of an exemplary articulated arm and locking member.

The present invention relates to devices for manipulation of bones and their associated soft-tissue structures including joints, muscles, tendons, ligaments, and nervous tissues. The devices use articulated arms that attach to bone and soft tissue to properly align bone and soft tissue for fixation. Locking members attached to the articulated arms are activated by buttons or switches to unlock the articulated arms for adjustment of the position of an attached bone and to lock the articulated arms for holding an attached bone in a stable position.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

Referring now to FIG. 1, an exemplary articulated arm 12 and locking member 20 are depicted. Articulated arm 12 comprises an elongate first shaft 14a having a distal end and a proximal end and an elongate second shaft 14b having a distal end and a proximal end. The proximal end of first shaft 14a and the distal end of 14b are hingedly connected by first hinge 16a and second hinge 16b, respectively. In various embodiments, the hinged connection can be any suitable hinge rotatable at least 180° and up to 360° degrees about a single axis, such as a joint hinge rotatable about a pin or a screw. Locking member 20 can be attached to articulated arm 12 and modulates the movement of the hinged connection between first hinge 16a and second hinge 16b.

Figure 2:
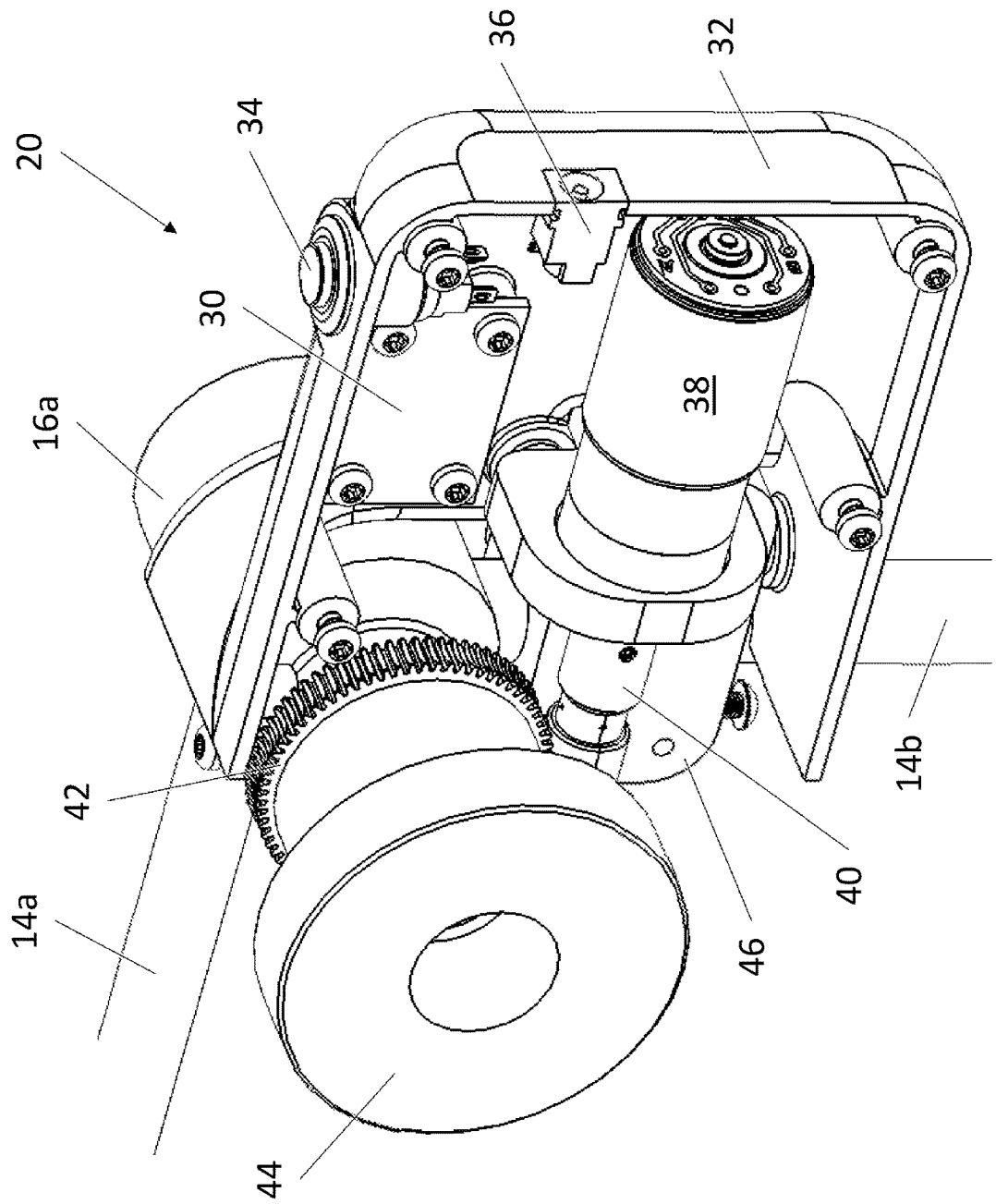
FIG. 2 depicts a perspective view of an exemplary locking member secured to an articulated arm. Portions of the locking member housing are removed to show the inner components of the locking member.
Figure 3:
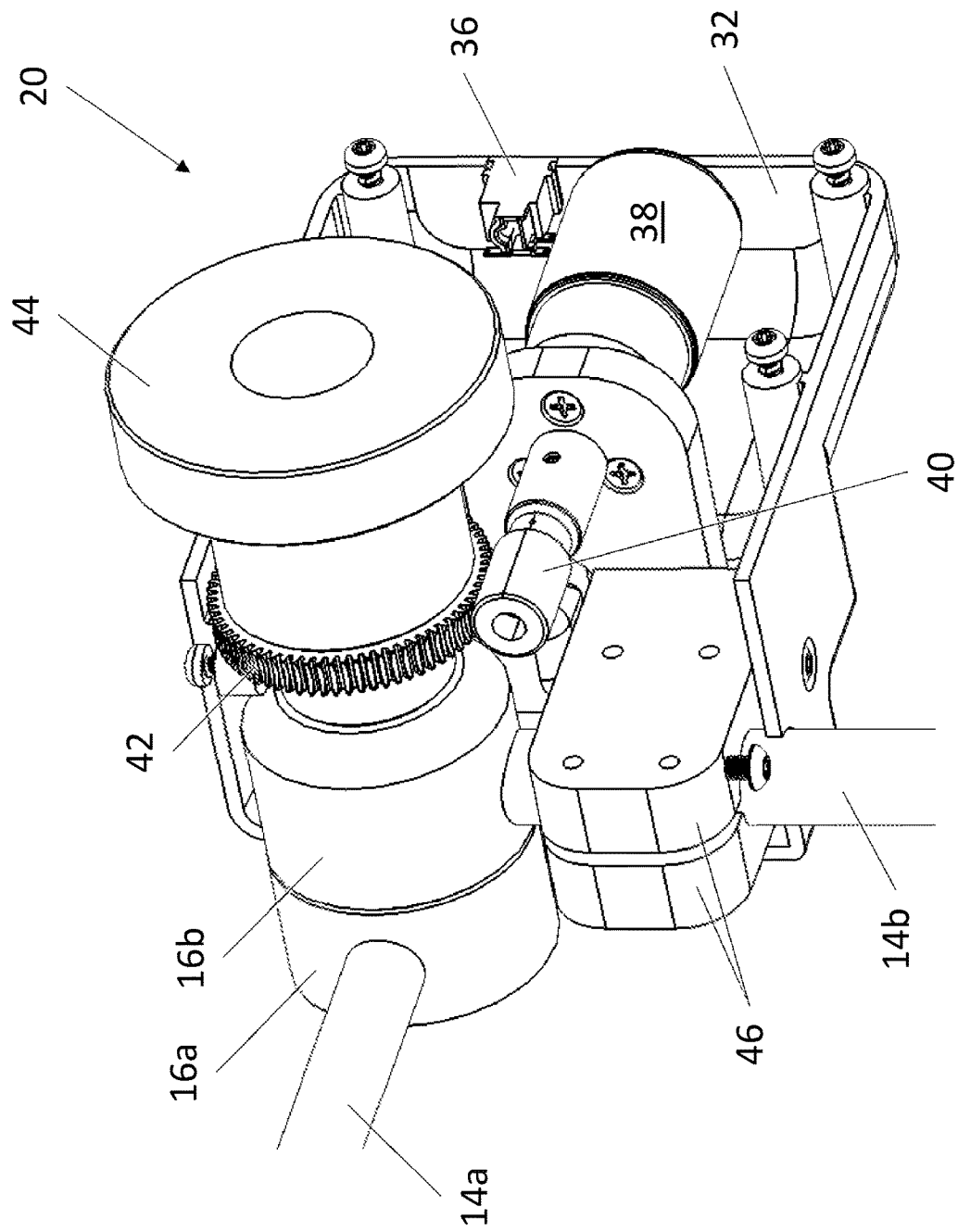
FIG. 3 depicts a perspective view of an exemplary locking member secured to an articulated arm. Portions of the locking member housing are removed to show the inner components of the locking member.

Referring now to FIG. 2 and FIG. 3, locking member 20 is depicted attached to articulated arm 12. Locking member 20 comprises housing 32, which is shown partially removed, to expose control unit 30, button 34, power connection 36, motor 38, worm gear 40, gear 42, knob 44, and clamp 46. Clamp 46 engages a shaft of articulated arm 12, such as second shaft 14b depicted in FIG. 3, to securely attach locking member 20 to articulated arm 12. The attachment of locking member 20 to articulated arm 12 positions knob 44 adjacent to the hinged connection between first hinge 16a and second hinge 16b, such that knob 44 is rotatable to tighten or loosen the hinged connection and reversibly lock the movement of articulated arm 12. In some embodiments, locking member 20 is integrated into articulated arm 12.

The rotation of knob 44 is coupled to motor 38 by way of gear 42 and worm gear 40. Worm gear 40 extends from motor 38 and is mated to gear 42, such that worm gear 40 and gear 42 translate the spinning of motor 38 to rotate knob 44. Worm gear 40 can be a single-start worm gear or a multi-start worm gear (not pictured). In some embodiments, worm gear 40 may be self-locking, such that knob 44 can only be rotated by activating motor 38. In other embodiments, worm gear 40 may be non-locking, such that an operator can manually rotate knob 44 independently from motor 38 activation. Motor 38 can be powered by an external power source connected to power connection 36, or by an internal power source, such as a battery.

In some embodiments, motor 38 is controllable using control unit 30 and one or more buttons 34. For example, one or more buttons 34 can be triggered by pressing, by capacitive touch sense, by grasping a grip, and the like. Depressing a button 34 activates motor 38 to drive worm gear 40 for a preset number of rotations in a first direction, which rotates gear 42 and knob 44 to unlock the hinged connection. Releasing a button 34 activates motor 38 to drive worm gear 40 for the same preset number of rotations in the opposite direction, which reverses the rotation of gear 42 and knob 44 to lock the hinged connection. An operator is thereby able to quickly and easily reposition an articulated arm 12 from a first locked position to a second locked position by depressing a button 34, moving the articulated arm 12 into the desired second locked position, and releasing the button 34. It should be understood that the present invention is not limited to the depicted locking mechanisms, and that any suitable reversibly locking mechanism is contemplated, such as a twist lock, an electromagnet, a drum brake, a disc brake, a clasp brake, a band brake, and the like.

In some embodiments, the one or more buttons 34 can modulate resistance in the hinged connection, such as with a potentiometer or pressure sensor coupled to a switch or trigger. Modulating the resistance in the hinged connection permits an operator to manipulate an articulated arm 12 without the articulated arm 12 loosening completely. In some embodiments, locking member 20 can comprise separate buttons 34 to perform the locking and unlocking functions. For example, a first button 34 can be depressed to unlock the hinged connection, and a second button 34 can be depressed to lock the hinged connection.

Figure 4:
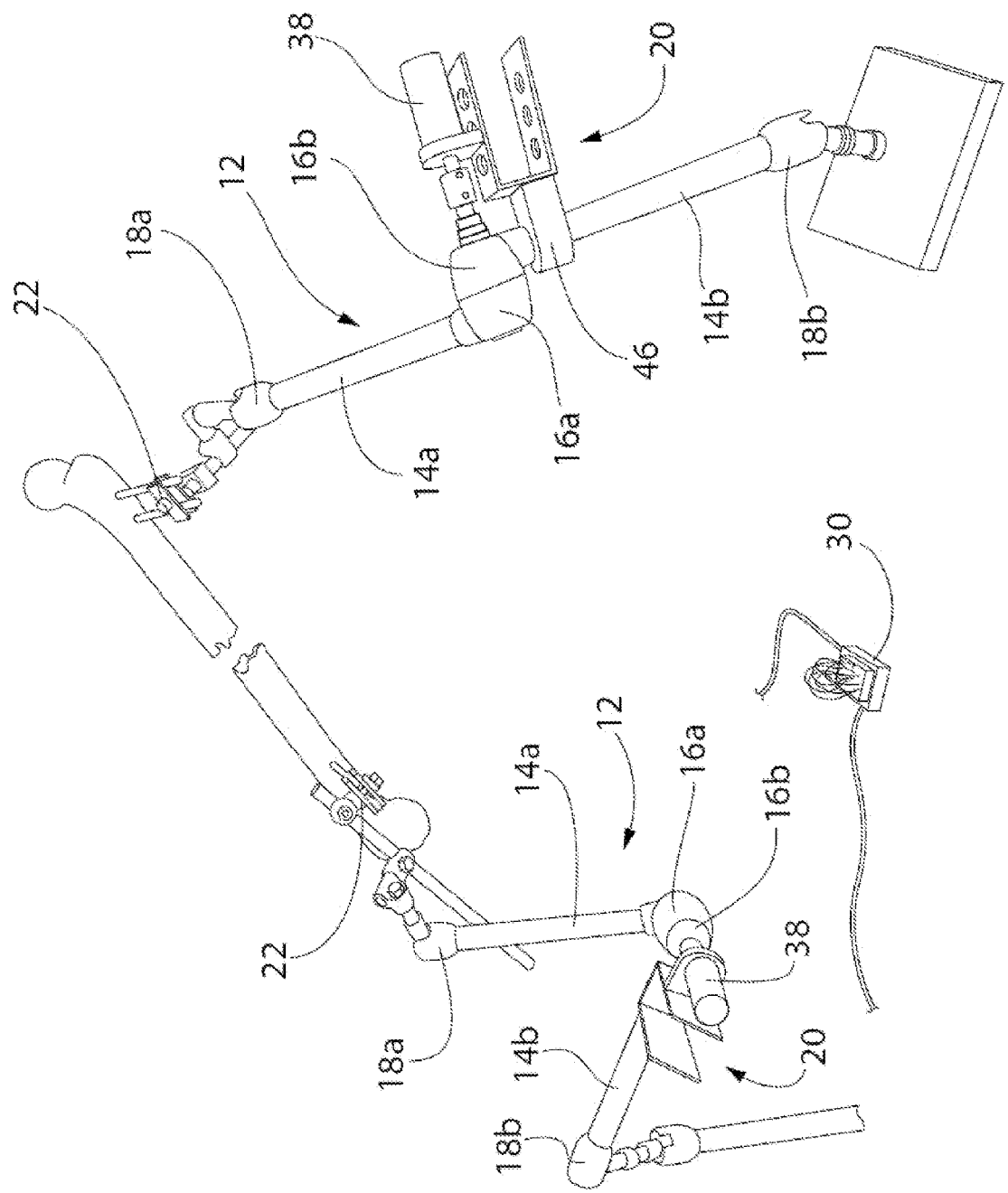
FIG. 4 depicts multiple exemplary articulated arms for manipulating bone and soft tissues.
Figure 5:
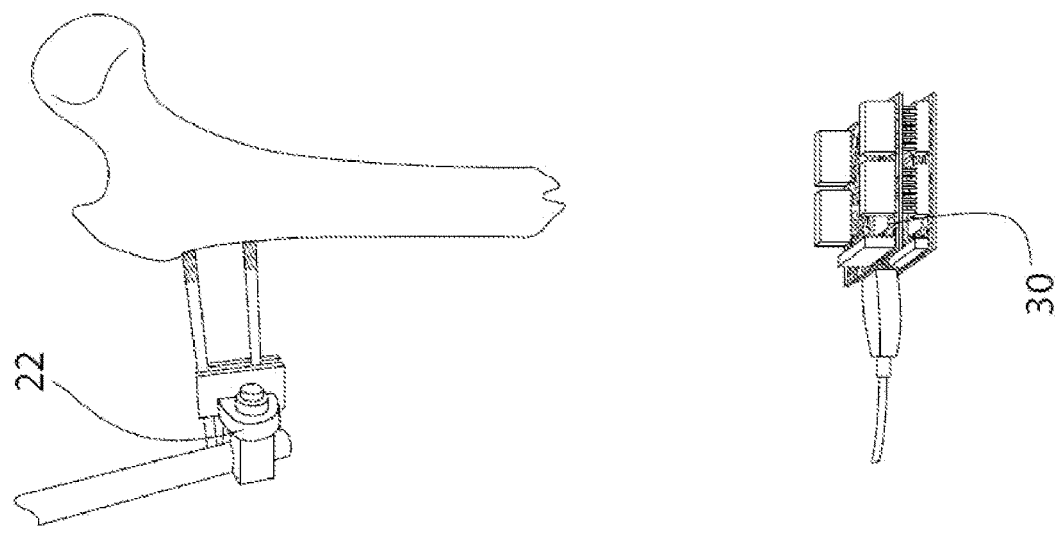
FIG. 5 depicts an exemplary articulated arm for manipulating bone and soft tissues.
Figure 5:
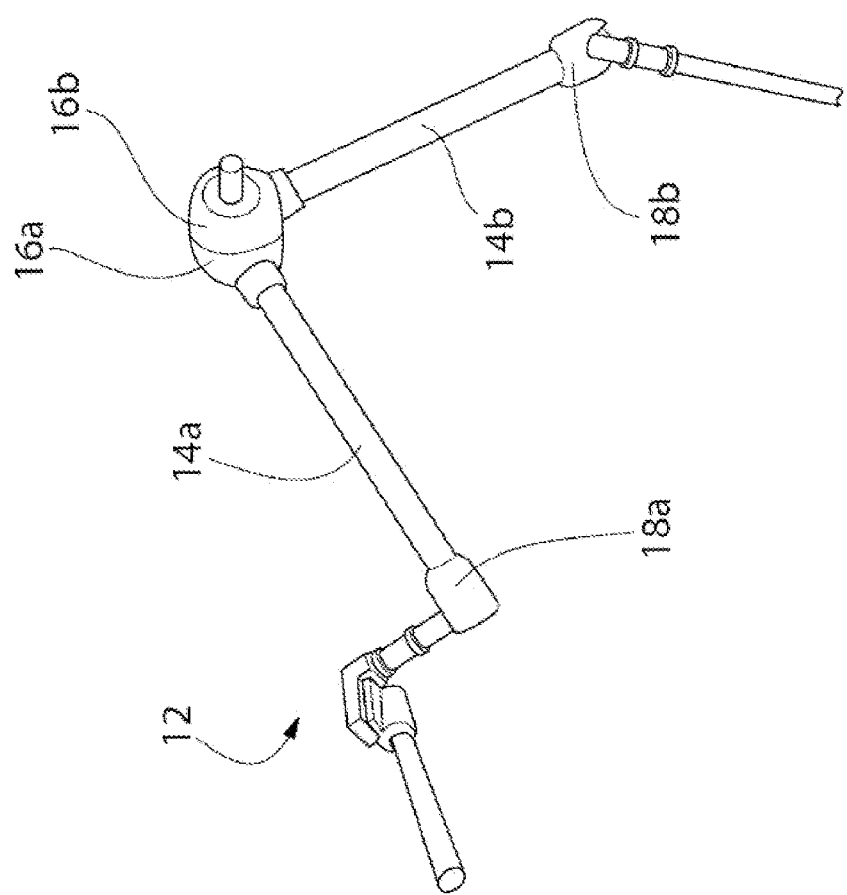

Referring now to FIG. 4 and FIG. 5, exemplary articulated arms 12 are depicted comprising one or more ball joints 18 and one or more fixing members 22. As described above, locking member 20 is secured to a shaft of articulated arm 12 by clamp 46 and comprises a motor 38 and a control unit 30 to coordinate the locking and unlocking of the hinged connection of each articulated arm 12 with the triggering of the one or more buttons 34. The distal end of first shaft 14a comprises a first ball joint 18a and the proximal end of second shaft 14b comprises a second ball joint 18b. First ball joint 18a is connected to fixing member 22. Fixing member 22 can comprise any suitable fixation element that is securable to a bone or soft tissue, such as one or more screw, nail, pin, plate, K-wire, clamp, vice, strap, and the like. Second ball joint 18b is connected to any suitable structure for stable anchoring of an articulated arm 12, such as the frame of an operating room bed.

In some embodiments, first shaft 14a and second shaft 14b each comprises a lumen running from their proximal and distal ends, wherein an actuating member (not pictured) positioned within the lumen engages locking member 20 to first ball joint 18a and second ball joint 18b, such that locking member 20 is capable of locking and unlocking movement in first ball joint 18a and second ball joint 18b. For example, the actuating member can be a cam rod, a rack and pinion mechanism, a wire-driven mechanism, an electromagnet, and the like that is controllable by locking member 20 to arrest movement in first ball joint 18a and second ball joint 18b. In some embodiments, the hinged connection, first ball joint 18a, and second ball joint 18b are simultaneously lockable. In other embodiments, the hinged connection, first ball joint 18a, and second ball joint 18b are individually lockable. In some embodiments, the resistance in the hinged connection, first ball joint 18a, and second ball joint 18b can be modulated using a potentiometer or a pressure sensor, as described elsewhere herein.

As contemplated herein, control unit 30 may comprise any computing device as would be understood by those skilled in the art, including microcontrollers, systems-on-chip (SOCs), desktop or mobile devices, laptops, desktops, tablets, smartphones or other wireless digital/cellular phones, televisions or other thin client devices as would be understood by those skilled in the art.

Control unit 30 is fully capable of sending commands to locking member 20 in response to depressing and releasing the one or more buttons 34 in each articulated arm 12. In certain embodiments, portions of locking member 20 may be computer operated, or in other embodiments, the entire locking member 20 may be computer operated. Control unit 30 can be configured to control parameters such as individual hinge and ball joint locking, simultaneous hinge and ball joint locking, resistance modulation, and the like.

In certain embodiments, each articulated arm 12 is motorized, such that movement in hinge 16, first ball joint 18a, second ball joint 18b, or combinations thereof is effected by motors (not pictured). Motorizing each articulated arm 12 may enhance the ease of positioning articulated arm 12. In some embodiments, control unit 30 can coordinate movement between two or more articulated arms 12. For example, a first articulated arm 12 may lock the position of a first tissue relative to the position of a second tissue held by a second articulated arm 12. Movement of the second articulated arm 12 causes control unit 30 to unlock and mirror the movement in the first articulated arm 12 to maintain the relative positions of the first and second tissues. In another example, an operator may effortlessly reposition a motorized articulated arm 12 from a first locked position to a second locked position by depressing a button 34, moving a motorized articulated arm 12 into the desired second locked position, and releasing the button 34, wherein the operator-directed motion of the motorized articulated arm 12 is supplemented by the motorization. Motorizing each articulated arm 12 may also allow an operator to remotely position each articulated arm 12. For example, an operator may reposition a motorized articulated arm 12 by remotely communicating with control unit 30 through wired or wireless means.

In various embodiments, articulated arm 12 further comprises one or more features for enhancing a surgical operation. For example, each articulated arm 12 may further comprise a sterile drape. Each articulated arm 12 may further comprise a holder for holding one or more additional instruments, including but not limited to endoscopes, laparoscopes, ultrasound probes, tubing, and the like.

As described elsewhere herein, the present invention provides devices for the enhanced manipulation of bones and their associated soft-tissue structures. Referring now to FIG. 6, an exemplary method 100 of aligning a fractured bone is depicted. Method 100 begins with step 102, wherein a first articulated arm of the present invention is provided. In step 104, the tissue fixing member of the first articulated arm is engaged to a first fragment of a fractured bone. In step 106, the hinge of the first articulated arm is locked. In step 108, a second articulated arm of the present invention is provided. In step 110, the tissue fixing member of the second articulated arm is engaged to a second fragment of the fractured bone. In step 112, the second fragment is aligned with the first fragment. In step 114, the hinge of the second articulated arm is locked.

It should be understood that the method is not limited to the use of two articulated arms. Any number of articulated arms may be provided to align as many fragments of a fractured bone as needed. It should also be understood that the method may be adapted for other tissues, such as muscle, skin, and organs, or adapted to position and align any object in a space.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A device for stably manipulating bone and soft tissue, comprising:
    an articulated arm comprising a first elongate shaft having a proximal and a distal end, a second elongate shaft having a proximal end and a distal end, and a hinge connecting the proximal end of the first shaft to the distal end of the second shaft;
    a tissue fixing member attached to the first shaft by a ball joint; and
    a locking member attached to the hinge;
    wherein the locking member reversibly locks all movement in the hinge and the ball joint simultaneously.
2. The device of claim 1, wherein the proximal end of the second shaft is connected to a stable frame by a ball joint.

3. The device of claim 1, wherein the proximal end of the second shaft is connected to one or more elongate shafts by one or more hinges, each hinge having a locking member attached thereto.

4. The device of claim 1, wherein the locking member is controlled by at least one button.

5. The device of claim 1, wherein the locking member is controlled by at least one touch sensor.

6. The device of claim 1, wherein the locking member is controlled by at least one squeezable grip.

7. The device of claim 1, wherein the locking member comprises a potentiometer or a pressure sensor.

8. The device of claim 7, wherein the locking member is capable of modulating the resistance in the hinge and the ball joint.

9. The device of claim 1, wherein the locking member comprises a lock selected from the group consisting of a twist lock, a geared knob, a clamp, an electromagnet, a drum brake, a disc brake, a clasp brake, and a band brake.

10. The device of claim 1, wherein the tissue fixing member is selected from the group consisting of a screw, a nail, a pin, a plate, a K-wire, a clamp, a vice, and strap.

11. The device of claim 1, wherein the hinge and ball joint are motorized.

12. The device of claim 11, wherein the locking, unlocking, and repositioning of the articulated arm is linked to the locking, unlocking, and repositioning of one or more additional articulated arms, such that locking, unlocking, and repositioning of one of the articulated arms is mirrored in each of the linked articulated arms.

13. The device of claim 11, wherein the motorized hinge and ball joint respond to externally induced movement of the articulated arm to supplement the positioning of the articulated arm.

14. The device of claim 11, wherein the motorized hinge and ball joint are remotely controllable.

15. The device of claim 1, further comprising a sterile drape.

16. The device of claim 1, further comprising a holder capable of attaching a surgical instrument.

17. A method of aligning a fractured bone; comprising the steps of:
   providing a first articulated arm of claim 1;
   engaging a first fragment of a fractured bone to the tissue fixing member of the first articulated arm;
   simultaneously locking the hinge and the ball joint of the first articulated arm;
   providing a second articulated arm of claim 1;
   engaging a second fragment of the fractured bone to the tissue fixing member of the second articulated arm;
   aligning the second fragment with the first fragment; and
   simultaneously locking the hinge and the ball joint of the second articulated arm.

18. The method of claim 17, further comprising the steps of:
   providing one or more articulated arms of claim 1;
   engaging one or more fragments of the fractured bone to the tissue fixing member of each of the one or more articulated arms;
   aligning the one or more fragments with the first and the second fragments; and
   simultaneously locking the hinges and ball joints of each of the one or more articulated arms.

* * * * *